United States Patent [19]

Higuchi et al.

[11] Patent Number: 5,225,750
[45] Date of Patent: Jul. 6, 1993

[54] MICROINJECTION APPARATUS, AND METHOD OF CONTROLLING MICROINJECTION

[75] Inventors: Toshiro Higuchi, Kanagawa; Ken-ichi Kudoh, Ibaraki; Atsushi Mimatsu, Ibaraki; Hisao Ueno, Ibaraki, all of Japan

[73] Assignee: Prima Meat Packers, Ltd., Japan

[21] Appl. No.: 588,261

[22] Filed: Sep. 26, 1990

[30] Foreign Application Priority Data

Oct. 2, 1989 [JP] Japan .................. 1-255197

[51] Int. Cl.$^5$ .............................. H02P 7/00
[52] U.S. Cl. .................................... 318/280
[58] Field of Search .............. 318/282–286, 318/599, 685–687, 116, 118, 127, 129; 310/311, 328, 342, 357, 17; 73/864.01, 864.16, 864.18, 864.23

[56] References Cited

U.S. PATENT DOCUMENTS

| | | | |
|---|---|---|---|
| 3,909,831 | 9/1975 | Marchio et al. | 318/696 |
| 4,273,122 | 6/1981 | Whitney et al. | 604/155 X |
| 4,367,435 | 1/1983 | Bailey et al. | 318/280 |
| 4,692,673 | 9/1987 | DeLong | 310/17 |
| 4,749,109 | 6/1988 | Kamen | 604/155 X |
| 4,812,724 | 3/1989 | Langer et al. | 318/599 |
| 4,833,384 | 5/1989 | Munro et al. | 318/687 |
| 4,842,493 | 6/1989 | Nilsson | 310/328 |
| 4,894,579 | 1/1990 | Higuchi et al. | 310/328 |
| 4,967,606 | 11/1990 | Wells et al. | 73/864.18 |
| 5,006,050 | 4/1991 | Cooke et al. | 604/153 X |

OTHER PUBLICATIONS

Rev. Sci. Instrum. 58, (1), Jan. 1987 pp. 54–57, "Dynamic Piezoelectric Translation Devices", D. W. Pohl.
Rev. Sci. Instrum. 59, (2) Feb. 1988 pp. 368–369, "Simple Piezoelectric Translation Device", EMCH et al.
Rev. Sci. Instrum. 59, (6), Jun. 1988, pp. 840–842, "Tracking Tunneling Microscopy", Pohl et al.
Mol. Gen. Genet (1986) 202, pp. 179–185 "Integration of Foreign DNA . . . " Exptl Cell Res. 87, (1974), pp. 403–406.

Primary Examiner—Jonathan Wysocki
Attorney, Agent, or Firm—Lorusso & Loud

[57] ABSTRACT

A microinjection apparatus according to the invention includes a microsyringe having a plunger, a rotative moving member which rotates together with a shaft, and a micromovement device mounted on the rotative moving member and having a piezoelectric/electro-strictive element equipped with an inertial member. Applying an electric signal to the micromovement device produces a driving force which causes the rotative moving member to rotate by a minute amount. As a result, the plunger is moved a minute amount in the axial direction to move a liquid within the microsyringe. Also provided is a microinjection apparatus which includes a microsyringe having an internal rotary plate serving as a plunger and attached to a center shaft, a rotative moving member which rotates together with the center shaft, and a micromovement device mounted on the rotative moving member and having a piezoelectric/electro-strictive element equipped with an inertial member. Applying an electric signal to the micromovement device produces a driving force which causes the rotative moving member to rotate by a minute amount. As a result, the rotary plate serving as the plunger is rotated a minute amount to move a liquid within the microsyringe. Further, the microinjection apparatus is so adapted that a micromovement device having a piezoelectric/electrostrictive element equipped with an inertial member is driven to drive a rectilinear moving member directly in a linear direction, thereby operating a plunger.

5 Claims, 6 Drawing Sheets

| OPERATION MODE | MICROMOVEMENT DEVICE | | ROTATIVE MOVING MEMBER |
|---|---|---|---|
| I. INJECTION | A | THRUSTING FORCE | CLOCKWISE ROTATION (IN FRONT VIEW) |
| | B | THRUSTING FORCE | |
| II. SUCTION | A | PULLING FORCE | COUNTER-CLOCKWISE ROTATION (IN FRONT VIEW) |
| | B | PULLING FORCE | |

| OPERATION MODE | MICROMOVEMENT DEVICE | ROTARY PLATE |
|---|---|---|
| I. INJECTION | A THRUSTING FORCE<br>B THRUSTING FORCE | CLOCKWISE ROTATION (IN FRONT VIEW) |
| II. SUCTION | A PULLING FORCE<br>B PULLING FORCE | COUNTER-CLOCKWISE ROTATION (IN FRONT VIEW) |

| OPERATION MODE | MICROMOVEMENT DEVICE | RECTILINEAR MOVING MEMBER |
|---|---|---|
| I. INJECTION | THRUSTING FORCE | ADVANCE |
| II. SUCTION | PULLING FORCE | RETRACT |

MICROINJECTION APPARATUS, AND METHOD OF CONTROLLING MICROINJECTION

BACKGROUND OF THE INVENTION

This invention relates to a microinjection apparatus of a micromanipulator for injecting liquids, and to a method of controlling microinjection performed by this apparatus.

In the realm of biotechnology, there is a field devoted to the artificial manipulation of genes, cells and the like to produce a body of new genetic information which is then utilized or studied. The subjects of study in this field are multifarious and include genes, cells, nuclei, fertilized embryos, tissue and protozoa. Micro-manipulation is available as a means of physically and mechanically manipulating those of these items that can be observed by an optical microscope. For example, micromanipulation is essential when injecting a foreign gene into a plant or animal cell or nucleus and analyzing the character manifesting mechanism of the gene, when segmenting an early embryo or a morula, implanting it in an adoptive parent and forming monozygotic multiples or when transplanting another individual into the cytoplasm of a fertilized egg to form a clone.

Figure 1:
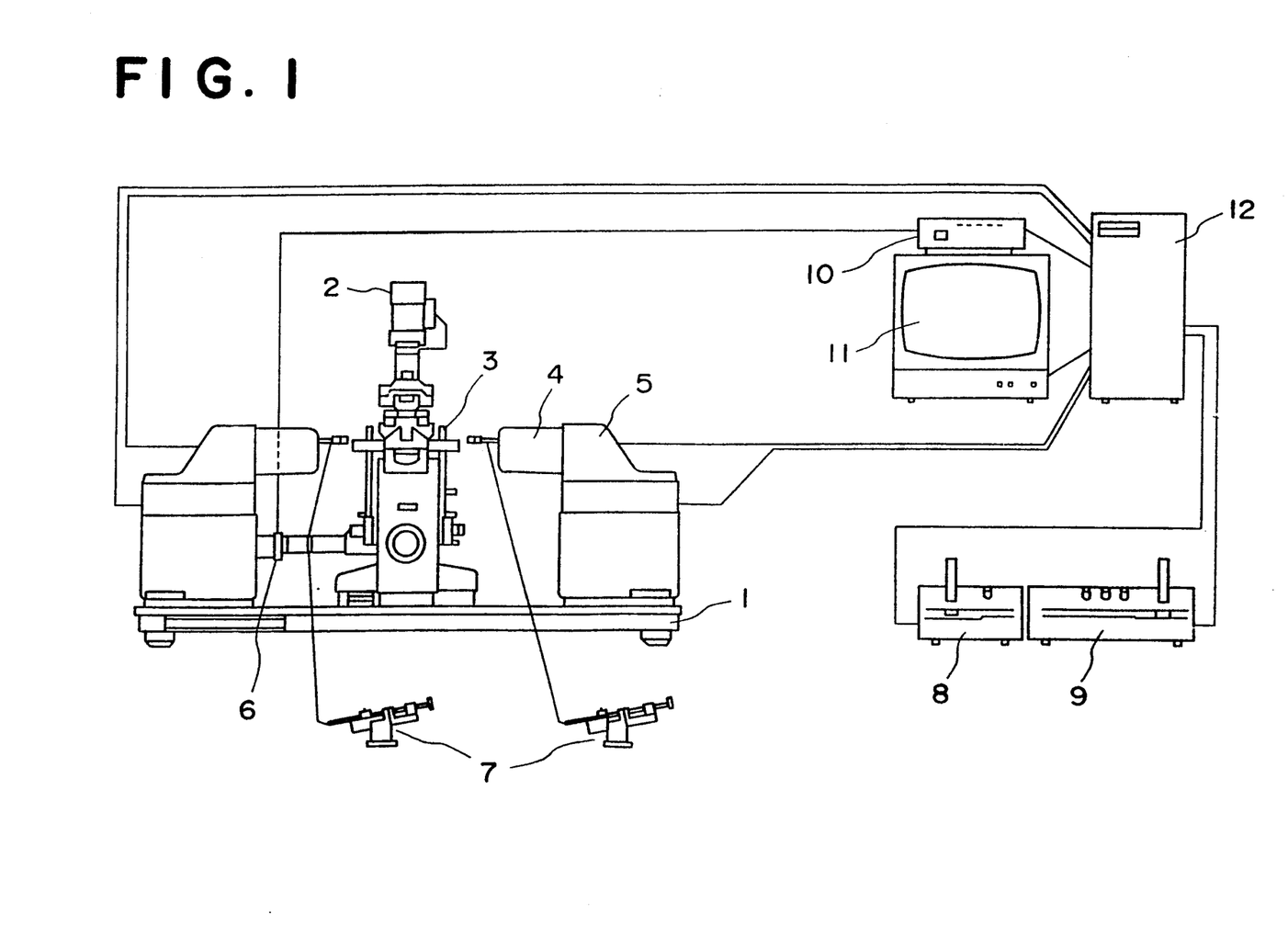
FIG. 1 is a diagram showing the overall arrangement of a micromanipulation system according to the prior art.

FIG. 1 is a diagram showing the overall arrangement of a micromanipulation system according to the prior art.

As shown in FIG. 1, the system includes a base 1, a microscope 2 disposed on the base 1, a position detector 3, a fine-movement unit 4, a coarse-movement unit 5, a television camera 6, a microinjector 7, a left control box 8, a right control box 9, a camera control unit 10, a video monitor 11 and a main control unit 12.

As illustrated in the Figure, the two control boxes 8, 9 are for manipulating the left and right fine-movement and coarse-movement units 4, 5 and for controlling various functions such as measurement of the amount of an injected liquid. The microscope 2 is provided with the TV camera 6 so that the state of a cell and the micromanipulation thereof can be observed by being projected on the video monitor 11.

Figure 2:
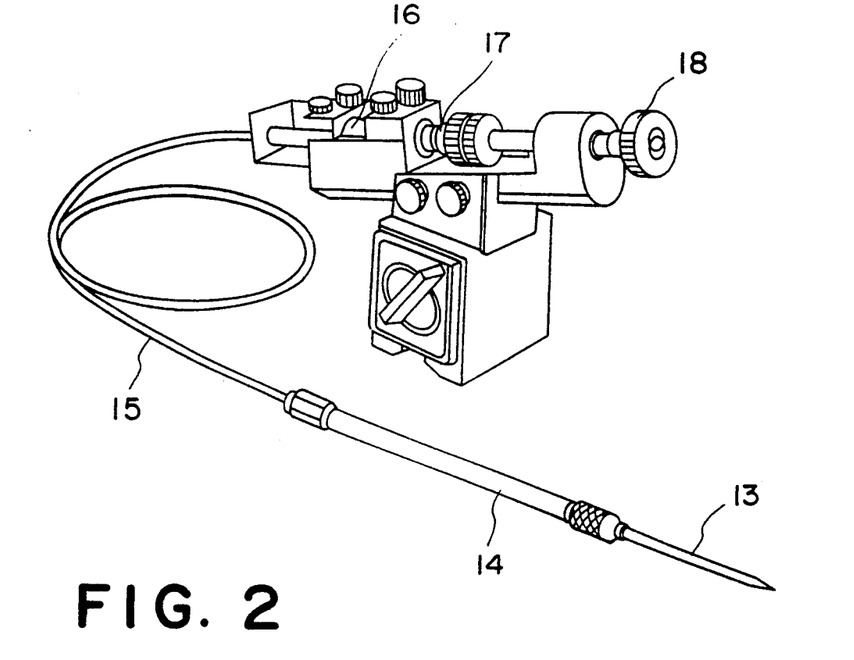
FIG. 2 is a perspective view showing a microinjection apparatus according to the prior art.

The arrangement of a conventional micromanipulation apparatus is as shown in FIG. 2. A miniature instrument 13 (e.g., a microneedle, micropipette or microelectrode) at the tip of the fine-movement unit is supported on a support rod 14, and a tube 15 is connected to the support rod 14. In order to make an injection into or a withdrawal from a cell, a plunger 17 of a microsyringe 16 is fed on threads by turning a knob 18, whereby positive or negative pressure can be applied.

This conventional microinjection apparatus will now be described in greater detail.

Many substances do not allow free passage through their cell membrane. Consequently, in order to examine the direct action of a substance on the protoplasm or organelle in the interior of a cell, microinjection in which the substance is injected into the cell through a capillary tube (micropipette) is the most direct method.

Though microinjection generally refers to an operation for injecting a substance into a cell, the same method can be utilized in a case where a liquid is made to act upon a specific region of a cell or tissue from the outside, or in a case where a portion of the protoplasm is sucked out of the interior of a cell or a minute object such as a small cell is sucked out. Methods of microinjection include a pressure method, in which a liquid placed inside a micropipette in advance is ejected from the micropipette by pressure, or a microelectrophoretic method, in which an electric current is passed through a micropipette and a substance within the micropipette is made to flow out along with the current.

Microinjection by way of the pressure method mentioned above will now be described.

Figure 3:
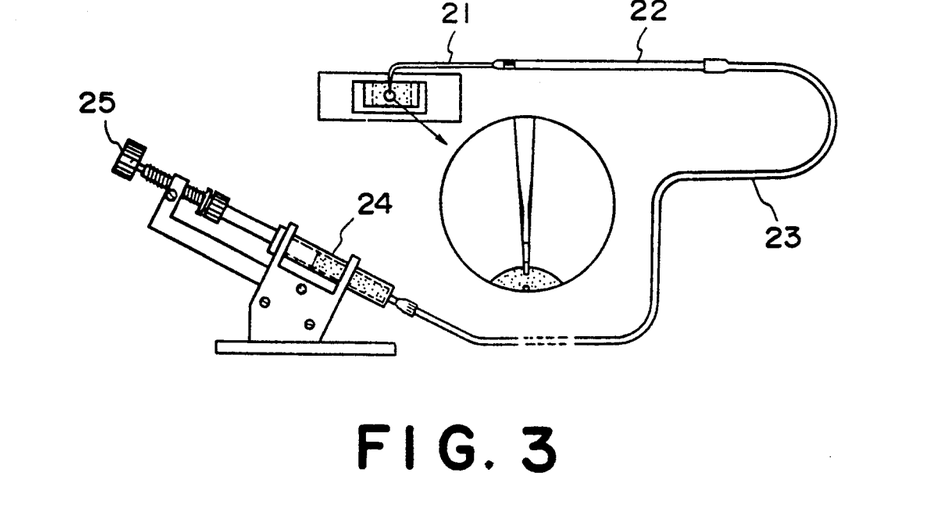
FIG. 3 is a diagram showing the arrangement of the microinjection apparatus according to the prior art.

As shown in FIG. 3, a microinjection apparatus relying upon the pressure method includes a micropipette (a miniature instrument) 21 attached to a hollow support rod 22, and a microsyringe 24 to which the support rod 22 is connected by a tube 23. The microsyringe 24 has the structure of a threaded-type syringe and is so adapted that positive or negative pressure can be applied by manually operating a knob 25.

Though different from a microinjection apparatus, an arrangement which can replace the above-described conventional micromanipulator has already been proposed in a U.S. patent application (U.S.S.N. 07/410,755) entitled "MICROMANIPULATOR" to which an invention entitled "APPARATUS FOR EFFECTING FINE MOVEMENT BY IMPACT FORCE PRODUCED BY PIEZOELECTRIC OR ELECTROSTRICTIVE ELEMENT" filed by the applicant of this application has been applied, wherein an inertial member is accelerated by applying a voltage to a piezoelectric/electrostrictive element and the reaction is utilized to cause movement of a miniature instrument, thereby making possible fine movement on the order of 10 nm–10 $\mu$m in a positive or negative direction. However, in the conventional microinjector described above, control of the microinjector depends upon the manual operation of a knob. As a result, the microinjector is difficult to operate and is unsatisfactory for accurate injection. In other words, in order to perform accurate injection, proficiency in the characteristics of the microinjector is required and a high level of skill is required also for the operating technique.

In addition, fine resolution cannot be obtained by an injection operation using a manually operated knob.

Furthermore, in case of the above-described microinjector, the tube connecting the microsyringe and the support rod is of considerable length. This requires a corresponding amount of space and slows down response by a commensurate amount.

SUMMARY OF THE INVENTION

An object of the present invention is to provide a compact microinjection apparatus capable of performing rapid, accurate injection and of promoting automation, as well as a method of controlling such microinjection.

According to the present invention, the foregoing object is attained by providing a microinjection apparatus of a micromanipulator for moving, by pressure, a liquid set in a miniature instrument, comprising a microsyringe having a plunger, a moving member provided on one end of the plunger, and a micromovement device mounted on the moving member and having a piezoelectric/electrostrictive element equipped with an inertial member.

The moving member is a rotative moving member and is capable of rotating both in forward and reverse directions.

Further, the moving member is a rectilinear moving member and is capable of moving in both forward and reverse directions.

According to the present invention, a microinjection control method of a micromanipulator is characterized in that a micromovement device having a piezoelectric-/electrostrictive element equipped with an inertial member is provided on a moving member that is provided on one end of the plunger of a microsyringe, and a liquid set in a miniature instrument is moved by pressure obtained by electrical drive of the micromovement device.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENTS

Embodiments of the present invention will now be described in detail with reference to the drawings.

With reference to FIGS. 4 through 7 to describe a first embodiment, there are shown a base 31, a stage 32, a support 33, an injection holder 34 the interior of which is cut to have female threads, rotative moving bodies 35, and a first micromovement device A comprising an inertial member 36 and a piezoelectric/electrostrictive element 37. Similarly, B represents a second micromovement device comprising an inertial member 38 and a piezoelectric/electrostrictive element 39. Numeral 40 denotes a microsyringe, 41 a miniature instrument, 42 a current feeding wire for driving the piezoelectric/electrostrictive elements 37, 39, and 43 a plunger inserted into and withdrawn from the microsyringe 40. Numeral 44 denotes a shaft to which the plunger 43 and rotative moving member 35 are fixed and whose outer periphery is formed to have male threads 44a. By virtue of the male threads 44a, the shaft 44 is threadedly engaged with the female threads on the inner periphery of the injection holder 34 and has a frictional function. Numeral 45 designates a liquid set inside the microsyringe 40, and numeral 50 denotes a control box for controlling the micromanipulator. A microinjection control switch is also provided on the control box 50. A position detector is shown at 51 and a microscope at 52.

The operation of the microinjection apparatus of the first embodiment will now be described with reference also to FIG. 14.

Microinjection is classified into two modes, namely an injection mode in which a chemical or the like is injected into a living body, and a suction mode in which a body fluid or the like is withdrawn from a living body. Though a mode in which cells, eggs or the like are held can also be mentioned, this can be regarded as the suction mode.

Figure 6:
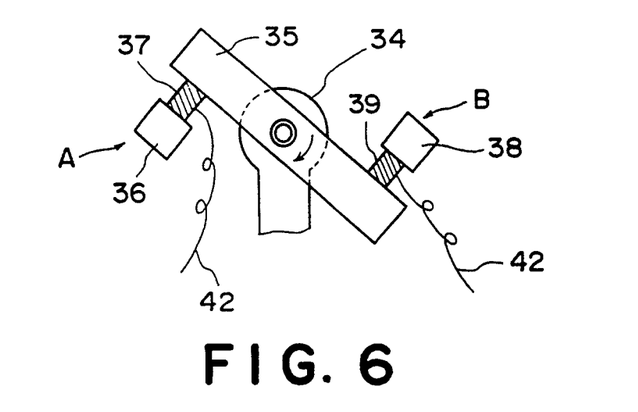
FIG. 6 is a front view of essential components of the microinjection apparatus.
Figure 7:
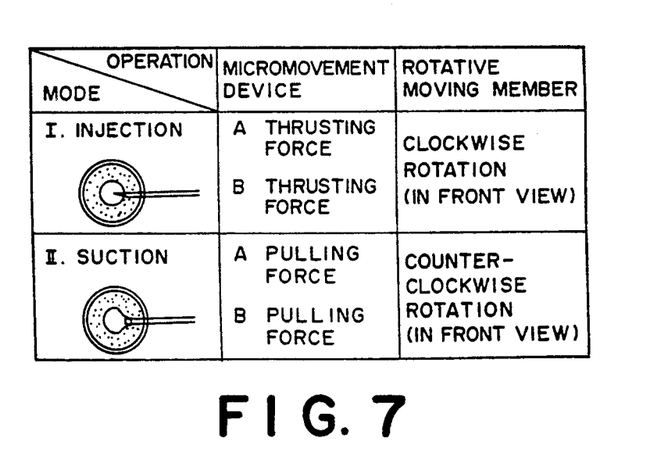
FIG. 7 is a diagram for describing the operating modes of the first embodiment of the present invention.

In a case where the injection mode is desired to be used, the operator presses a Mode I push-button of the microinjection switch provided on the control box 50. When this is done, a thrusting force is produced in both the first and second micromovement devices A, B, as a result of which the rotative moving member 35 rotates a minute amount in the clockwise direction, as shown in FIG. 6, thereby advancing the plunger 43 and the liquid 45. This produces positive pressure in the microsyringe 40.

In a case where the suction mode is desired to be used, the operator presses a Mode II push-button of the microinjection switch provided on the control box 50. When this is done, a pulling force is produced in both the first and second micromovement devices A, B, as a result of which the rotative moving member 35 rotates a minute amount in the counter-clockwise direction, as shown in FIG. 6, thereby retracting the plunger 43 and the liquid 45. This produces negative pressure in the microsyringe 40.

In the foregoing embodiment, the arrangement is such that balance is achieved using the first and second micromovement devices A, B. However, it is permissible to adopt an arrangement in which a single micromovement device is used. In such case, either the operation of the thrusting force or pulling force of the single micromovement device is used selectively.

A second embodiment of the present invention will now be described.

Figure 8A:
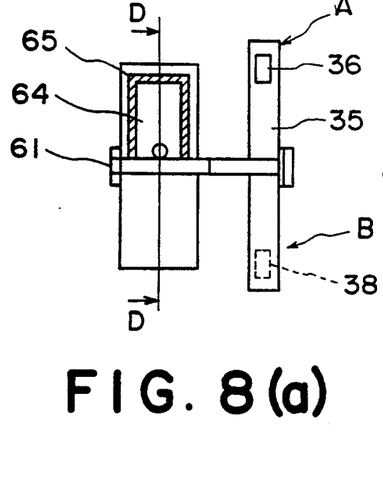
FIG. 8 is a diagram showing the main components of a second embodiment of a microinjection apparatus according to the present invention.
Figure 8B:
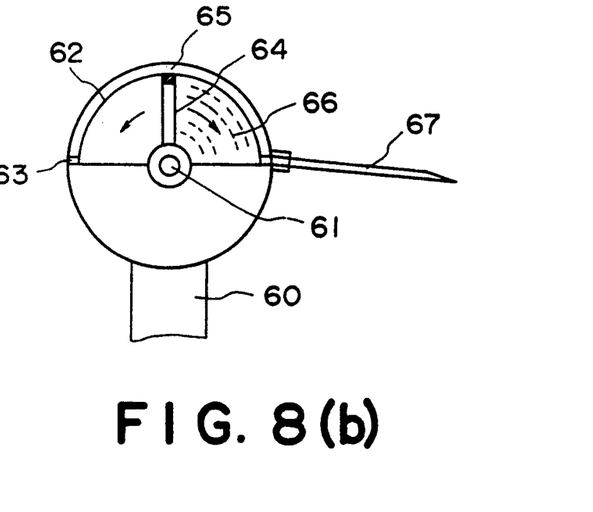
Figure 9:
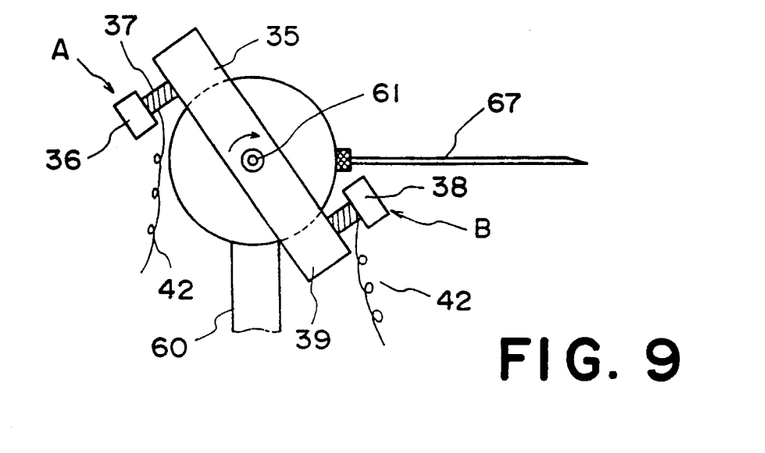
FIG. 9 is a front view of essential components of this microinjection apparatus.
Figure 10:
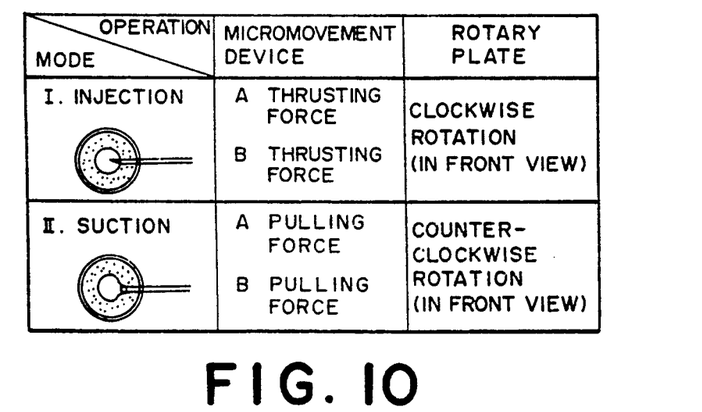
FIG. 10 is a diagram for describing the operating modes of the second embodiment of the present invention.

Shown in FIGS. 8 through 10 are an injection holder 60, a center shaft 61, a microsyringe 62, a vent hole 63 formed in the microsyringe 62, a rotary plate 64 accommodated within the microsyringe 62 and serving as a rotating plunger, a seal member 65 provided at the periphery of the rotary plate 64, a liquid 66 set inside the microsyringe 62, and a miniature instrument 67 attached to the microsyringe 62. The rotative moving member and micromovement device attached to the center shaft 61 are similar to those described above. Therefore, the same reference characters are assigned to these components and a detail description thereof is deleted.

The operation of the microinjection apparatus of the second embodiment described above will now be described with reference to FIG. 14.

Figure 4:
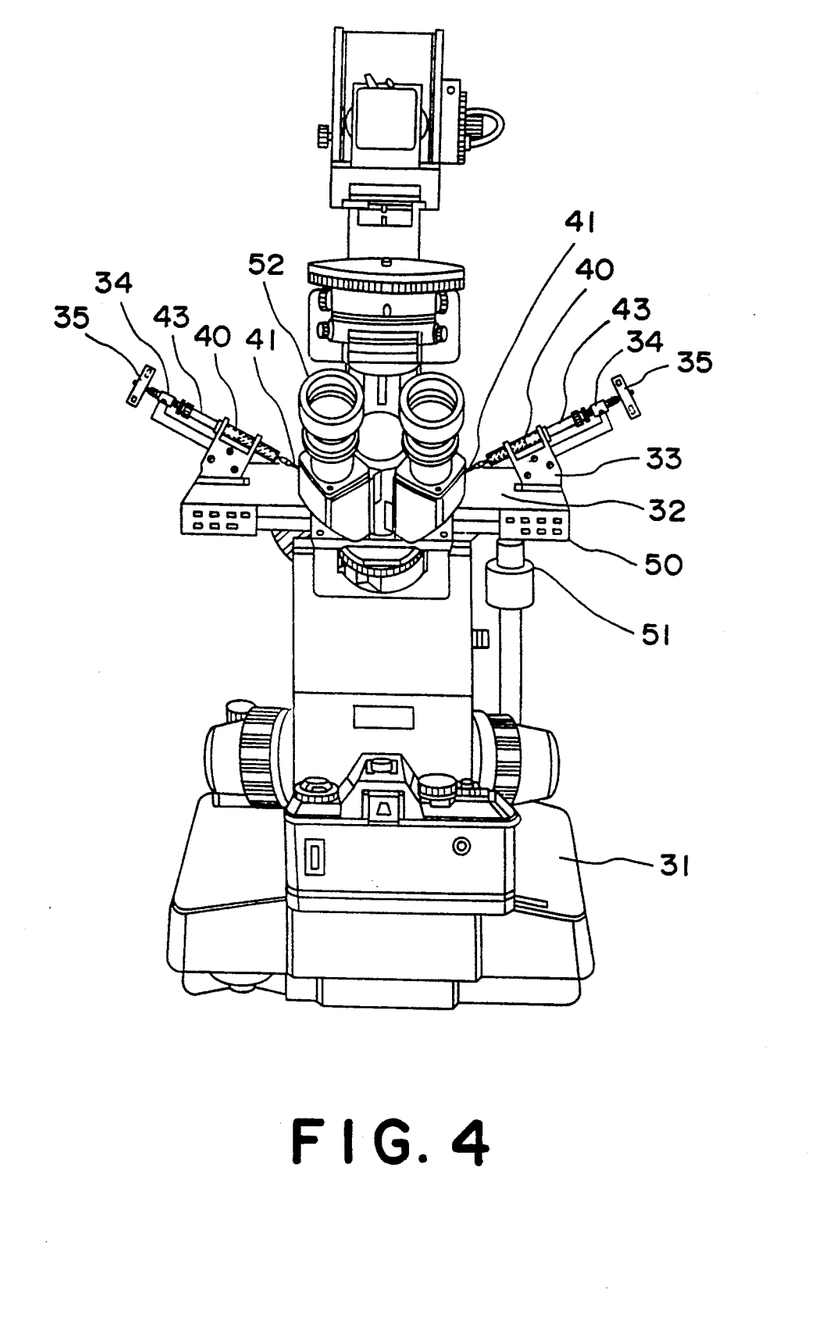
FIG. 4 is a diagram showing the overall arrangement of a first embodiment of a microinjection apparatus according to the present invention.
Figure 5:
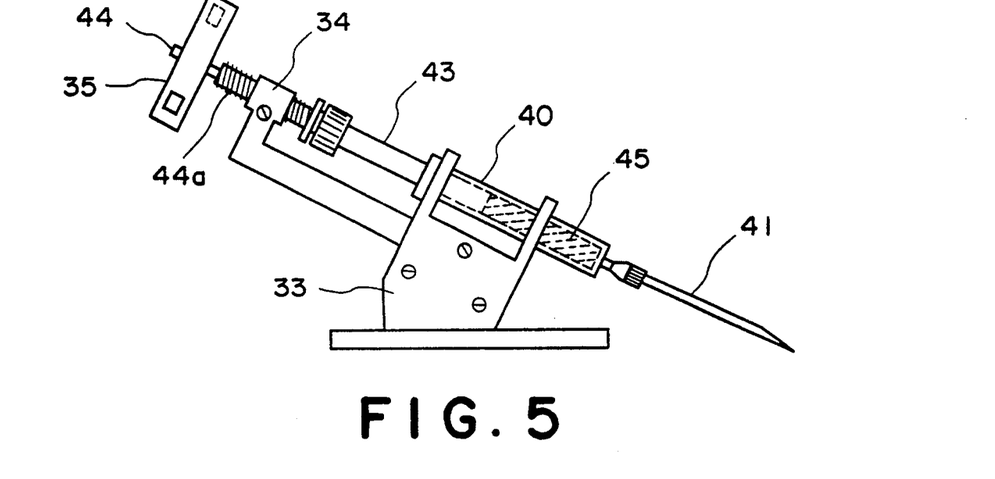
FIG. 5 is a diagram showing the construction of principal components of this microinjection apparatus.

In a case where the injection mode is desired to be used, the operator presses the Mode I push button of the microinjection switch provided on the control box 50 (see FIG. 4). When this is done, a thrusting force is produced in both the first and second micromovement devices A, B, as a result of which the rotative moving member 35 rotates a minute amount in the clockwise direction, as shown in FIG. 9, accompanied by the rotary plate 64, which also rotates a minute amount in the clockwise direction. This causes the liquid 66 to advance, thereby producing positive pressure in the microsyringe 62. In this case, negative pressure does not develop in the space within the microsyringe 62 since the latter is provided with the vent hole 63.

In a case where the suction mode is desired to be used, the operator presses the Mode II push-button of the microinjection switch provided on the control box 50 (see FIG. 4). When this is done, a pulling force is produced in both the first and second micromovement devices A, B, as a result of which the rotative moving member 35 rotates a minute amount in the counter-clockwise direction, as shown in FIG. 9, accompanied by the rotary plate 64, which also rotates a minute amount in the counter-clockwise direction. This causes the liquid 66 to retract, thereby producing negative pressure in the microsyringe 62.

A third embodiment of the present invention will be described next.

Figure 11:
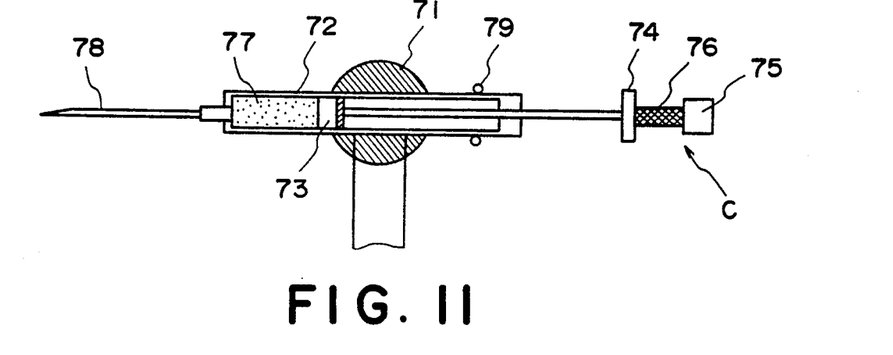
FIG. 11 is a diagram showing the main components of a third embodiment of a microinjection apparatus according to the present invention.
Figure 12:
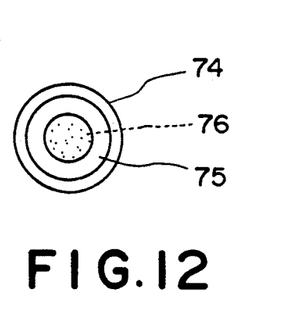
FIG. 12 is a front view of essential components of this microinjection apparatus.
Figure 13:
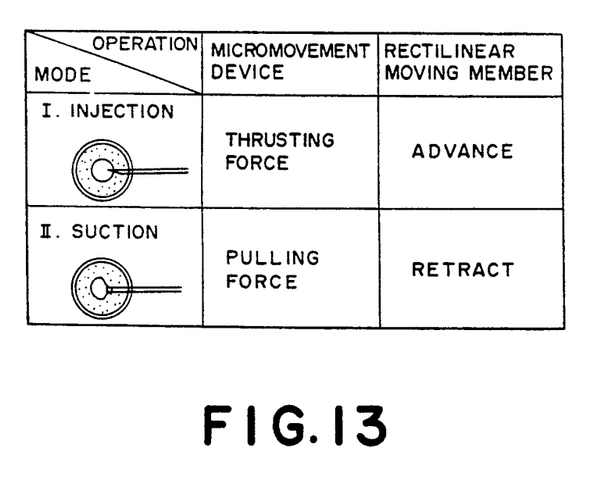
FIG. 13 is a diagram for describing the operating modes of the third embodiment of the present invention.

Shown in FIGS. 11 through 13 are an injection holder 71, a microsyringe 72, a plunger 73, a rectilinear moving member 74 and a third micromovement device C, which comprises an inertial member 75 and a piezoelectric/electrostrictive element 76. Numeral 77 denotes a liquid set inside the microsyringe 72, and 78 a miniature instrument attached to the tip of the microsyringe 72. The rear end portion of the microsyringe 72 is formed to include a slit for preventing vibration of the plunger 73, and a flexible ring 79 is resiliently fitted onto this rear end portion about its outer periphery. This frictional function can be so adapted that the free end of a leaf spring whose other end is attached to a fixed portion comes into abutting contact with the rear end portion of the microsyringe 72.

The operation of the microinjection apparatus of the third embodiment will now be described with reference to FIG. 14.

Here also microinjection is classified into two modes, namely the injection mode and the suction mode.

In a case where the injection mode is desired to be used, the operator presses the Mode I push button of the microinjection switch provided on the control box 50 (see FIG. 4). When this is done, a thrusting force is produced in the third micromovement device C, as a result of which the rectilinear moving member 74 moves a minute amount in the leftward direction in FIG. 11. This causes the plunger 73 and the liquid 77 to advance, thereby producing positive pressure in the microsyringe 72.

In a case where the absorption mode is desired to be used, the operator presses the Mode II push-button of the microinjection switch provided on the control box 50 (see FIG. 4). When this is done, a pulling force is produced in the third micromovement device C, as a result of which the rectilinear moving member 74 moves a minute amount in the rightward direction in FIG. 11. This causes the plunger 73 and the liquid 77 to retract, thereby producing negative pressure in the microsyringe 72.

Figure 14:
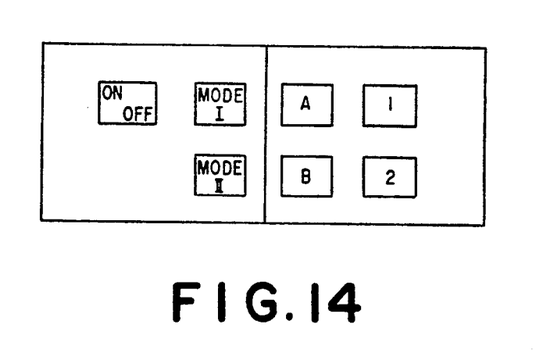
FIG. 14 is a front view of a control box according to the present invention.

Besides having the aforementioned mode selection switch, the front side of the control box shown in FIG. 14 is provided with a power supply on/off switch and with switches for various control operations in addition to microinjection control.

The arrangement and structure of the moving member in the micromovement device can be modified in various ways.

As described in detail hereinabove, the present invention is capable of providing the following effects:

(1) Rapid, precise injection control can be carried out.

(2) Micromovement on the order of 10 nm–10 $\mu$m in the positive and negative directions can be achieved by driving the micromovement devices, and therefore manipulation having a very high resolution is possible.

(3) Since the tubing is short, the overall apparatus can be made compact and response can be improved.

(4) The space required for the injection apparatus is small and the apparatus can be mounted simply on a stage.

(5) The operator is capable of performing the injection operation without being required to have a high level of skill, and the operator is freed from the mental fatigue that accompanied operation in the past. In addition, the apparatus of the invention is capable of reducing the amount of labor.

As many apparently widely different embodiments of the present invention can be made without departing from the spirit and scope thereof, it is to be understood that the invention is not limited to the specific embodiments thereof except as defined in the appended claims.

What is claimed is:

1. A microinjection apparatus for moving, by pressure, a liquid through a miniature instrument, said apparatus comprising:
   (a) a microsyringe having a plunger; and
   (b) reversible driving means for driving said plunger into said microsyringe in an injection mode and for withdrawing said plunger from said microsyringe in a suction mode, said driving means comprising:
      i. a driven member provided on one end of said plunger;
      ii. at least one elongated piezoelectric/electrostrictive element having one end fixed to said driven member; and
      iii. an inertial member fixed to the end of said elongated piezoelectric/electrostrictive element opposite said one end.

2. The microinjection apparatus according to claim 1, wherein said reversible driving means further comprises a rotatable member capable of rotation both in forward and reverse directions, said rotatable member being interposed between said plunger and said driven member.

3. The microinjection apparatus of claim 2 wherein said driven member is elongated and has its center fixed to said rotatable member and wherein two of said elongated piezoelectric/electrostrictive elements are mounted on said driven member at opposite ends thereof, said elongated piezoelectric/electrostrictive elements being mounted in an opposing relationship for reversibly driving said driven member and said rotatable member.

4. The microinjection apparatus of claim 3 wherein said rotatable member is treadably mounted, coaxially with said plunger.

5. The microinjection apparatus according to claim 1, wherein said driven member moves rectilinearly.

* * * * *

UNITED STATES PATENT AND TRADEMARK OFFICE
CERTIFICATE OF CORRECTION

PATENT NO.   : 5,225,750
DATED        : July 6, 1993
INVENTOR(S)  : Higuchi et al It is certified that error appears in the above-indentified patent and that said Letters Patent is hereby corrected as shown below:

The title page, showing the illustrative figure should be deleted to be replaced with the attached title page.

Signed and Sealed this

Seventeenth Day of May, 1994

Attest:

BRUCE LEHMAN

*Attesting Officer*     *Commissioner of Patents and Trademarks*

United States Patent [19]

Higuchi et al.

[11] Patent Number: 5,225,750
[45] Date of Patent: Jul. 6, 1993

[54] MICROINJECTION APPARATUS, AND METHOD OF CONTROLLING MICROINJECTION

[75] Inventors: Toshiro Higuchi, Kanagawa; Ken-ichi Kudoh, Ibaraki; Atsushi Mimatsu, Ibaraki; Hisao Ueno, Ibaraki, all of Japan

[73] Assignee: Prima Meat Packers, Ltd., Japan

[21] Appl. No.: 588,261

[22] Filed: Sep. 26, 1990

[30] Foreign Application Priority Data

Oct. 2, 1989 [JP] Japan .................. 1-255197

[51] Int. Cl.⁵ .............................................. H02P 7/00
[52] U.S. Cl. .................................................. 318/280
[58] Field of Search ............................... 318/282–286, 318/599, 685–687, 116, 118, 127, 129; 310/311, 328, 342, 357, 17; 73/864.01, 864.16, 864.18, 864.23

[56] References Cited

U.S. PATENT DOCUMENTS

| 3,909,831 | 9/1975 | Marchio et al. | 318/696 |
| 4,273,122 | 6/1981 | Whitney et al. | 604/155 X |
| 4,367,435 | 1/1983 | Bailey et al. | 318/280 |
| 4,692,673 | 9/1987 | DeLong | 310/17 |
| 4,749,109 | 6/1988 | Kamen | 604/155 X |
| 4,812,724 | 3/1989 | Langer et al. | 318/599 |
| 4,833,384 | 5/1989 | Munro et al. | 318/687 |
| 4,842,493 | 6/1989 | Nilsson | 310/328 |
| 4,894,579 | 1/1990 | Higuchi et al. | 310/328 |
| 4,967,606 | 11/1990 | Wells et al. | 73/864.18 |
| 5,006,050 | 4/1991 | Cooke et al. | 604/153 X |

OTHER PUBLICATIONS

Rev. Sci. Instrum. 58, (1), Jan. 1987 pp. 54–57, "Dynamic Piezoelectric Translation Devices", D. W. Pohl.
Rev. Sci. Instrum. 59, (2) Feb. 1988 pp. 368–369, "Simple Piezoelectric Translation Device", EMCH et al.
Rev. Sci. Instrum. 59, (6), Jun. 1988, pp. 840–842, "Tracking Tunneling Microscopy", Pohl et al.
Mol. Gen. Genet (1986) 202, pp. 179–185 "Integration of Foreign DNA . . . " Exptl Cell Res. 87, (1974), pp. 403–406.

Primary Examiner—Jonathan Wysocki
Attorney, Agent, or Firm—Lorusso & Loud

[57] ABSTRACT

A microinjection apparatus according to the invention includes a microsyringe having a plunger, a rotative moving member which rotates together with a shaft, and a micromovement device mounted on the rotative moving member and having a piezoelectric/electrostrictive element equipped with an inertial member. Applying an electric signal to the micromovement device produces a driving force which causes the rotative moving member to rotate by a minute amount. As a result, the plunger is moved a minute amount in the axial direction to move a liquid within the microsyringe. Also provided is a microinjection apparatus which includes a microsyringe having an internal rotary plate serving as a plunger and attached to a center shaft, a rotative moving member which rotates together with the center shaft, and a micromovement device mounted on the rotative moving member and having a piezoelectric/electro-strictive element equipped with an inertial member. Applying an electric signal to the micromovement device produces a driving force which causes the rotative moving member to rotate by a minute amount. As a result, the rotary plate serving as the plunger is rotated a minute amount to move a liquid within the microsyringe. Further, the microinjection apparatus is so adapted that a micromovement device having a piezoelectric/electrostrictive element equipped with an inertial member is driven to drive a rectilinear moving member directly in a linear direction, thereby operating a plunger.

5 Claims, 6 Drawing Sheets